United States Patent

Somogyi et al.

[11] Patent Number: 5,288,863
[45] Date of Patent: Feb. 22, 1994

[54] PROCESS FOR THE PREPARATION OF HIGH-PURITY 1-(3-CHLORO-PHENYL)-4-METHYL-7,8-DIMETHOXY-5H-2,3-BENZODIAZEPINE

[75] Inventors: György Somogyi; Péter Botka; Gyula Horváth; Antal Simay; Roózsa Gyenge; Imre Moravcsik; Ernó Orbán; Tamás Hámori; Jeno Korösi; Csilla Kiss; Tibor Balogh; Mária Bidló née Iglói; née Dievald Uskert, all of Budapest, Hungary

[73] Assignee: Egis Gyogyszergyar Rt., Budapest, Hungary

[21] Appl. No.: 878,379

[22] Filed: May 4, 1992

[30] Foreign Application Priority Data

May 3, 1991 [HU] Hungary .................. 1482/91

[51] Int. Cl.⁵ .......................... C07D 243/02
[52] U.S. Cl. .......................... 540/567
[58] Field of Search .......................... 540/567

[56] References Cited

U.S. PATENT DOCUMENTS 4,322,346 3/1982 Korosi et al. .................. 540/567

OTHER PUBLICATIONS

Lang, Chemical Abstract 105:133915k (1986).
Korosi, Chemical Abstract 93:168318d (1980).
Christian et al., editors, *Instrumental Analysis*, 2nd ed. (1978), p. 56, (Allyn and Bacon, Inc.).
*Kirk–Othmer Encyclopedia of Chemical Technology*, 3rd ed. (1981), p. 939, (John Wiley and Sons).

*Primary Examiner*—John M. Ford
*Assistant Examiner*—Philip Datlow
*Attorney, Agent, or Firm*—Beveridge, DeGrandi, Weilacher & Young

[57] ABSTRACT

The invention relates to a process for the preparation of 1-(3-chlorophenyl)-4-methyl-7,8-dimethoxy-5 $\underline{H}$-2,3-benzodiazepine of formula (I)

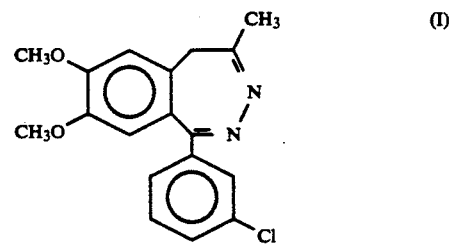

in high purity and in a quality suitable for pharmaceutical purposes.

According to the invention the reaction of 1 mole of 2-acetonyl-3'-chloro-4,5-dimethoxybenzophenone of formula (II)

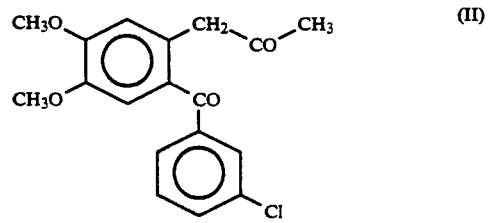

with 3-7 moles of hydrazine hydrate in an organic solvent or in a mixture of organic solvents at a temperature between 15° C. and 85° C. is carried out in the absence of air oxygen, optionally in the presence of water. The crude product is then recrystallized from an aliphatic alcohol containing 1 to 5 carbon atom(s).

4 Claims, No Drawings

PROCESS FOR THE PREPARATION OF HIGH-PURITY 1-(3-CHLORO-PHENYL)-4-METHYL-7,8-DIMETHOXY-5H-2,3-BENZODIAZEPINE

This invention relates to a process for the preparation of 1-(3-chlorophenyl)-4-methyl-7,8-dimethoxy-5H-2,3-benzodiazepine of formula (I)

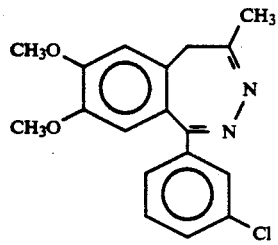

in high purity and in a quality suitable for pharmaceutical purposes.

In the present patent application 1-(chlorophenyl)-4-methyl-7, 8-dimethoxy-5 H-2,3-benzodiazepine is considered to be of high purity if—according to high pressure liquid chromatographic examinations—the total contamination content thereof does not exceed 0.3% by mass.

The 5H-2,3-benzodiazepine derivatives possess generally valuable central nervous activity, such as antiaggressive, antidepressant and narcotizing effects. According to preclinical and clinical trials one of them, the 1-(3-chlorophenyl)-4-methyl-7,8-dimethoxy derivative is to be considered as a drug candidate (Hungarian patent specifications Nos. 179,018 and 191,702).

Several methods are known in the art for the preparation of 5H-2,3-benzodiazepines. Among them the process disclosed by the Hungarian patent specification No. 191, 702 seems to be the most favourable one considering either the high yield or the feasibility on industrial scale. According to this process 1-(3-chlorophenyl)-4-methyl-7, 8-dimethoxy-5H-2,3-benzodiazepine of formula (I) is produced by reacting 2-acetonyl-3'-chloro-4, 5-dimethoxybenzophenone of formula (II) [hereinafter: diketone of formula (II)]

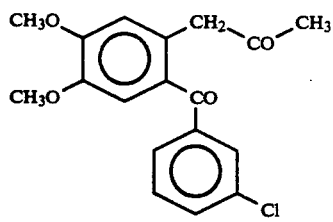

with 3-7 moles of hydrazine hydrate calculated on one mole of diketone, at a temperature between −20° C. and +110° C. The reaction time depends on the temperature and varies between 1 and 168 hour(s). The yield of the crude product isolated from the reaction mixture amounts to 80–85% and the efficiency of recrystallization of the crude product from isopropanol is about 90%.

According to our investigations the 1-(3-chlorophenyl)-4-methyl-7, 8-dimethoxy-5H-2,3-benzodiazepine of formula (I) thus obtained contains 3 characteristic contaminations. Semiquantitive thin layer chromatographic examinations show [adsorbent: silica gel HF$_{254}$,eluent: a 2:8 mixture of benzene and ethyl acetate, evaluation in UV light]that the total amount thereof is about 1%. The contaminating components were separated by preparative layer chromatography and identified by spectroscopic methods (IR, NMR, MS).

Said contamintions proved to be the following compounds:

1. 1-(chlorophenyl)-4-methyl-5-hydroxy-7,8-dimethoxy-5 H-2, 3- benzodiazepine of formula (III), m.p.: 181° –184° C. (from isopropanol)
2. 1-(chlorophenyl)-4-methyl-8-methoxy-5H-2,3-benzodiazepine of formula (IV), m.p.: 128°–129° C. (from isopropanol)
3. 1-(3-chlorophenyl)-3-methyl-6,7-dimethoxyisoquinolinone of formula (V), m.p,: 163°–165 ° C. (from abs. ethanol)

High pressure liquid chromatographic examinations showed that the recrystallized 1-(3-chlorophenyl)-4-methyl-7, 8-dimethoxy-5H-2,3-benzodiazepine of formula (I) generally contained 0.1–0.3% by mass of 8-monomethoxy derivative of formula (IV)

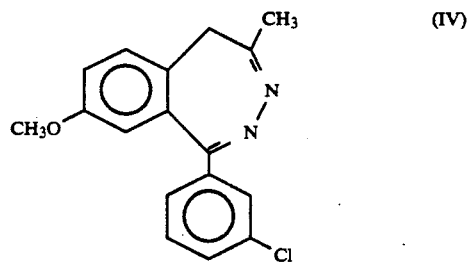

and isoquinoline derivative of formula (V),

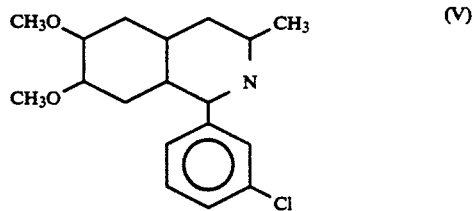

each. The 5-hydroxybenzodiazepine of formula (III)

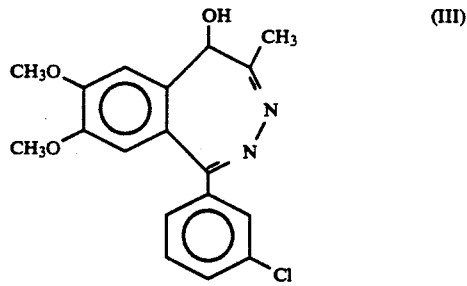

can be detected generally in an amount of 0.5–1.0% by mass in the crude product obtained according to the method described in Hungarian patent specification No. 191,702, but in certain cases—even when using the same starting substances and applying apparently the same reaction conditions—the amount thereof may be surprisingly as high as 2–3% by mass.

The crude product containing such a high amount of contaminations cannot be purified by the usual recrystallization. In our experiments a great number of solvents and solvent mixtures [such as alcohols comprising 1 to 3 carbon atom(s), acetic acid esters, aliphatic ketones, tetrahydrofuran, benzene, the mixtures thereof and the mixture of these solvents formed with dimethylformamide, chlorinated hydrocarbons, water and acetic acid] have been tried. According to these experiments the 5-hydroxybenzodiazepine contamination of formula (III) practically separates together with the 1-(3chlorophenyl)-4-methyl-7,8-dimethoxy-5H-2,3-benzodiazepine of formula (I).

When the product containing 2% by mass of 5-hydroxybenzodiazepine of formula (III) is purified by fractional crystallization and recrystallized from a 30-fold volume of ethyl acetate related to the mass of the product, a 1st fraction of 52.4% yield containing 3% by mass and a 2nd fraction of 40.6% yield containing 0.6% by mass of 5-hydroxybenzodiazepine derivative of formula (III) are obtained. In order to decrease the 5-hydroxybenzodiazepine content at least below 0.5% by mass, fraction 2 is to be subjected again to fractional crystallization. This step, however, results in an unacceptably high loss of substance.

The aim of the invention is to provide simple and effective methods ensuring the preparation of 1-(3-chlorophenyl)-4-methyl-7, 8-dimethoxy-5H-2,3-benzodiazepine in a high purity and quality suitable for pharmaceutical purposes.

Two methods have been found to comply with the above requirements.

a) One method is successful to improve the process starting from the diketone of formula (II) and hydrazine hydrate by eliminating or considerably reducing the formation of contaminations of formulae (III) to (V) during the process.

b) An other method is effective in the purification of the compound of formula (I) contaminated due to the defects in the effectuation of the process for the preparation of a high-purity product starting from the diketone of formula (II) and/or owing to the accidental contaminations of the starting diketone.

Method a) of the invention is based on the surprising recognition that if the reaction of the diketone of formula (II) with hydrazine hydrate is carried out in the absence of air oxygen, practically no 5-hydroxy-benzodiazepine is formed in the reaction. It was not at all aforeseen that while hydrazine hydrate being present in the reaction mixture in a large excess —altough it is a strong reducing agent—cannot prevent the oxydation side-reactions leading to the formation of 5-hydroxybenzodiazepine of formula (III), the formation of this compound can completely be prevented in the absence of air oxygen. Besides, it has been found that by choosing appropriate reaction conditions—such as temperature or solvent—the formation of the contaminating compounds of formulae (IV) and (V) can be prevented, too.

Thus, according to an aspect of the present invention there is provided a process for the preparation of 1-(3-chlorophenyl)-4-methyl-7,8-dimethoxy-5H-2,3-benzodiazepine of formula (I) in high purity and in a quality suitable for pharmaceutical purposes by reacting 1 mole of 2-acetonyl-3'-chloro-4,5-dimethoxybenzophenone of formula (II) with 3 to 7 moles of hydrazine hydrate in an organic solvent or in a mixture of organic solvents, at a temperature between 15° C. and 85° C. and subsequently recrystallizing the crude product from an aliphatic alcohol containing to 1 to 5 carbon atom(s), which comprises carrying out the reaction of the 2-acetonyl-3'-chloro-4,5-dimethoxybenzophenone with hydrazine hydrate in the absence of air oxygen, optionally in the presence of water.

The starting 2-acetonyl-3'-chloro-4,5-dimethoxybenzophenone of formula (II) can be prepared as described in Hungarian patent specification No. 194,529.

As solvent, monovalent or polyvalent aliphatic alcohols comprising to 1 to 5 carbon atom(s), dimethylformamide, dimethyl sulfoxide, chlorinated hydrocarbons, peroxide-free dioxane, tetrahydrofuran, the mixtures thereof or, in case of water-miscible solvents, the mixtures of these solvents with water can be used. It is preferable—but not necessary—to deoxygenate the solvent by simple boiling before it is used. The reaction vessel can be deoxygenated by known methods, e.g. by evacuating or flushing the air space of the equipment with an inert gas. For this purpose preferably nitrogen or a noble gas can be used.

According to a preferred embodiment of the process of the invention the diketone of formula (II) is suspended in an aliphatic alcohol comprising to 1 to 5 carbon atom(s) optionally containing water, the vessel is deoxygenated with nitrogen or argon and 98–100% hydrazine hydrate is added to the suspension while stirring. Then the inert gas atmosphere is maintained and the mixture is reacted at a temperature between 25° C. and 70° C. The reaction time—considering the extreme temperature values—lasts for about 78 and 3 hours, respectively. The reaction mixture is then optionally diluted with distilled water and the excess of hydrazine hydrate is neutralized with acetic acid. The crystalline product spearating upon cooling is filtered, washed with an aqueous alcohol and dried. The yield of the crude product amounts to 85–90%.

The crude product is recrystallized—related to the mass thereof—from 10 to 12 parts by volume of ethanol or isopropanol. The solution is optionally treated with charcoal.

Method b) is based on the surprising recognition that the hydroxy group of 5-hydroxybenzodiazepine of formula (III)—although it is not attached to an aromatic ring—has under certain conditions a phenolic character. In case of the process according to the invention this means that if 13-chlorophenyl)-4-methyl-7, 8-dimethoxy-5H-2,3-benzodiazepine of formula (I) contaminated with 5-hydroxybenzodiazepine of formula (III) is dissolved in an appropriate solvent and treated with an alkali hydroxide, alkali carbonate or alkali alcoholate and then the compound of formula (I) is crystallized from the solution, this latter compound separates in a high purity and yield, while the corresponding alkali derivative of the compound of formula (III), owing to its better solubility, remains dissolved. The recrystallization according to this process is an effective method for the purification of the desired compound of formula (I) contaminated with isoquinolines of formula (V), too.

Thus, according to a further aspect of the present invention there is provided a process for the purification of 1-(3-chlorophenyl)-4-methyl-7,8-dimethoxy-5H-2,3-benzodiazepine of formula (I) containing contamination(s) of formula (V) and/or particularly of formula (III), which comprises dissolving the contaminated compound of formula (I) in an appropriate solvent, treating it with an alkali hydroxide, alkali carbonate or alkali alcoholate, preferably at the boiling point of the solvent, crystallizing the compound of formula (I) from the solution and optionally recrystallizing it from an aliphatic alcohol comprising 1 to 5 carbon atom(s).

Any solvent or solvent mixture suitable for the recrystallization of the benzodiazepine of formula (I) and inert towards the applied alkali hydroxide, carbonate or alcoholate can be used for the reaction, supposing that at least a 0.005 mole/l solution can be prepared from the said alkali compounds in the said solvent. It is preferable to use straight or branched chained mono- or polyvalent aliphatic alcohols comprising 1 to 5 carbon atom(s) or mixtures thereof as solvent. The solvents are not required to be anhydrous, but on increasing the water content the effectiveness of the purifying process is decreasing. (Even on applying a solvent containing 10% of water for the recrystallization a significant improvement of quality can be achieved.)

As alkali hydroxides and carbonates the easily available sodium or potassium compounds can be used. As alkali alcoholate sodium or potassium alcoholates prepared from straight or branched chained alcohols comprising 1 to 4 carbon atom(s) are preferably applied. They can be obtained either from the commerce or prepared in situ from an appropriate alcohol and alkali metal. The upper limit of the amount of the alkali compounds used for the reaction is restricted by the solubility thereof in the solvent in question, but at least 1 mole of alkali compound is to be used for 1 mole of 5-hydroxybenzodiazepine contamination of formula (III). (Using more than 35 moles of alkali compound does not imply advantages.)

According to a preferred embodiment of the purifying process of the invention 5 to 30 moles of an alkali hydroxide, alkali carbonate or alkali alcoholate related to 1 mole of 5-hydroxybenzodiazepine are added to a 12-fold volume of isopropanol or 18-fold volume of tert-butanol related to the mass of the compound of formula (I) containing 1 to 3% by mass of 5-hydroxybenzodiazepine, the solution thus obtained is heated to boiling and the crude benzodiazepine of formula (I) to be purified is dissolved in it. From the solution thus obtained the compound of formula (I) is crystallized by cooling, the product is filtered, washed successively with isopropanol or tert-butanol and distilled water until neutral and dried. Thus, the contamination content of the substance is decreased by about one order of magnitude, and the yield of the process amounts to 88 to 95%. For pharmaceutical use the product is preferably recrystallized again from a 12-fold volume of isopropanol or more preferably from ethanol. This recrystallization can be performed with a yield of 94 to 97%. According to HPLC examinations the product thus obtained contains not more than 0.3% of contaminations, generally 5-hydroxybenzodiazepine of formula (III) and 8-monomethoxy derivative of formula (IV).

The methods according to the invention render possible the preparation of 1-(3-chlorophenyl)-4-methyl-7, 8 dimethoxy-5H-2,3-benzodiazepine containing not more than 0.3% of contamination. This result is achieved by simple measures, that is by carrying out the reaction in the absence of air oxygen and by choosing an appropriate temperature. Said measures, while they result in a considerable improvement in the quality of the product, do not cause losses in the yield compared with the known processes, they even make possible the stabilization of the yield at a high level. The purification process according to the invention represents a simple and effective method for the purification of 1-(3-chlorophenyl)-4-methyl-7, 8-dimethoxy-5H-2,3-benzodia contaminated for any reason, containing especially 5-hydroxybenzodiazepine of formula (III).

Both processes according to the invention are economically feasible on industrial scale, too, and the product prepared or purified by these methods is suitable for phrmaceutical use based on its purity grade of 99.7 to 100.0%.

The product thus obtained can be converted directly into a pharmaceutical composition, preferably subsequent to a micronization ensuring a mean particle size of below $25/\mu$.

Further details of the processes are to be found in the following Examples without limiting the scope of protection to the said Examples.

Example 1

1-(3-chlorophenyl)-4-methyl-7,8-dimethoxy-5H-2,3-benzodiazepine 20.0 (0.060 mole) of 2-acetonyl-3'-chloro-4,5-dimethoxybenzophenone (II) are added to 70 ml of isopropanol and air is expelled from the flask with a nitrogen stream. Then 18.0 ml (0.367 mole) of 98–100% hydrazine hydrate are added within 1–2 minutes, under slow stiriing, and while a nitrogen atmosphere is maintained in the vessel the reaction mixture is stirred at 28°–32° C. for 78 hours. It is cooled to 20° C., diluted with 70 ml of distilled water, then 17.1 ml of glacial acetic acid are added. A crystalline product gets separated from the orange-red solution within 1–2 minutes. The rystalline suspension is stirred at 0°–5° C. for 4 hours, filtered, washed with a 1:1 mixture of isopropanol and water and dried at 40° C. Thus 17.85 g of crude product are obtained. M.p.: 168.5°–170° C. The crude product is dissolved in 214 ml of boiling isopropanol, the solution is treated with charcoal and cooled to 0°–5° C. under stirring. The separated product is filtered off, washed with isopropanol of 0°–5° C. and dried at 40° C. Thus 16.1 g (80.2% related to the diketone of formula II) of the desired compound are obtained in the form of white crystals which, according to HPLC examination, do not contain a measurable amount of contamination. The product is suitable for pharmaceutical purposes either in this form or—if desired—subsequent to a micronization resulting in an average particle size of below $25/\mu$. M.p.: 168°–169° C.

Example 2

1-(3-chlorophenyl)-4-methyl-7,8-dimethoxy-5H-2,3-benzodiazepine 20.0 g (0.060 mole) of 2-acetonyl-3'-chloro-4,5-dimethoxybenzophenone (II) are portionwise added to 100 ml of a 9:1 mixture of methanol and water, and air is expelled from the flask with an argon stream. Then 17.6 ml (0.363 mole) of 98–100% hydrazine hydrate are added under slow stirring, within 1–2 minutes, and while an argon atmosphere is maintained in the vessel the reaction mixture is boiled (68° C.) for 3 hours. It is cooled to 20° C. and 16.5 ml of glacial acetic acid are added. The crystalline suspension thus obtained is diluted with 80 ml of distilled water and stirred at 0°–5° C. for 4 hours. The separated product is filtered off, washed with a 1:1 mixture of methanol and distilled water and dried at 40° C. Thus 18.0 g of crude product are obtained. M.p.: 166°–169° C. The crude product is dissolved in 216 ml of boiling abs. ethanol, the solution is tretated with charcoal, washed with ethanol of 0°–5° C. and dried at 40° C. Thus 15.4 g (78.1% by mass, related to the diketone of formula II) of the desired compound are obtained, which—according to HPLC examination—does not contain any contamination.

M.p.: 168°–169° C.

Example 3

1-(3-chlorophenyl)-4-methyl-7,8-dimethoxy-5H-2,3-benzodiazepine

One proceeds as described in Example 2 except that the crude product is recrystallized from 216 ml of isopropanol. Thus 16.43 g (83.1%, related to the diketone of formula II) of 1-(3-chlorophenyl)-4-methyl-7, 8-dimethoxy-5H-2,3-benzodiazepine are obtained. According to HPL examinations the product contains 0.12 by mass of monomethoxy derivative of formula (IV).

M.p.: 168°–170° C.

Example 4

Purification of contaminated 1-(3-chlorophenyl)-4-methyl-7, 8-dimethoxy-5H-2,3-benzodiazepine containing 1.4% by mass of 5-hydroxybenzodiazepine contamination of formula (III) according to HPLC examinations are dissolved in 600 ml of isopropanol containing potassium hydroxide in an amount of 0.39 g/100 ml. When the dissolution is complete, the mixture is cooled to 0°–5° C. and allowed to crystallize at the same temperature for 4 hours. The separated crystals are filtered off, washed until neutral with isopropanol of 0° to 5° C. and distilled water and dried to constant weight at 40° C. Thus 47.6 g of the desired compound are obtained which are recrystallized from a 12-fold amount by volume of isopropanol. Yield. 46.2 g (92.4%). According to HPLC examinations the product contains 0.20% by mass of 5-hydroxybenzodiazepine contamination of formula (III).

M.p.: 168–169 ho$^C$.

Example 5

Purification of contaminated 1-(3-chlorophenyl)-4-methyl7, 8dimethoxy-5H-2,3-benzodiazepine 0.15 g (1.3 mmole) of potassium tert-butylate are added to 90 ml of tert-butanol, and 5.0 g (15 mmoles) of 1-(3-chlorophenyl)-4-methyl-7,8-dimethoxy-5H-2,3-benzodiazepine of formula (I) containing—according to HPLC examinations—1.5% by mass (0.22 mmoles) of 5-hydroxybenzodiazepine contamination of formula (III) are dissolved in the mixture at the boiling point thereof. Then it is cooled to 25°–27° C. and allowed to crystallize at the same temperature for 4 hours. The separated crystals are filtered off and washed to neutral with tert-butanol of 25°–27° C. and with distilled water, then they are dried to constant weight at 40° C. Thus 4.4 g of white crystalline product are obtained which are recrystallized from a 12-fold volume of ethanol related to the mass of the product to yield 4.2 g (84.0%) of the desired compound containing—according to HPLC examinations - 0.12% by mass of 5-hydroxybenzodiazepine contamination of formula (III).

M.p.: 167°–167.5° C.

Example 6

Purification of contaminated 1-(3-chlorophenyl)-4-methyl-7, 8-dimethoxy-5H-2,3-benzodiazepine 0.5 g (5.0 mmoles) of sodium ethylate are dissolved in 70 ml of isopropanol, then 50 g (15 mmoles) of 1-(3-chlorophenyl)-4-methyl-7, 8-dimethoxy-5H-2,3-benzodiazepine of formula (I) containing—according to HPLC examinations—1.5% by mass of 5-hydroxybenzodiazepine contamination of formula (III) are dissolved in it under boiling. When the dissolution is complete, the reaction mixture is cooled to 0°–5° C. and stirred at the same temperature for 4 hours. The separated crystals are filtered off, washed with isopropanol of 0°–5° C. and with distilled water to neutral and dried to constant weight at 40° C. Thus 4.6 g of white crystalline product are obtained which are recrystallized from a 12-fold volume of isopropanol related to the mass of the product to yield 4.3 g (86.0%) of the desired compound containing —according to HPLC examinations - 0.22% by mass of 5-hydroxybenzodiazepine contamination of formula (III). M.p.: 167.5°–168.5 ° C.

Example 7

Examination of the the possible contaminations of 1-(3-chlorophenyl)4-methyl-7,8-dimethoxy-5H-2,3-benzodiazepine The possible contaminations of the compound of formula (I) are separated by HPLC using a Nucleosil $C_{18}10/\mu(4\times250$ mm) column with a moving phase of 60:40 mixture of acetonitrile and a 0.1M acetate buffer (pH=4). The detection is carried out at 230 nm using an UV detector. The chromatograms are recorded on a Recording Integrator.

In the following Table the relative retention time and relative signal intensity of the possible contaminations of the compound of formula (I) measured at 230 nm and related to the peak of the main product (I) are shown.

| Compound | Relative retention time | Relative signal intensity |
| --- | --- | --- |
| 1-(3-Chlorophenyl)-4-methyl-5-hydroxy-7,8-dimethoxy-5H-2,3-benzodiazepine (III) | 0.57 | 0.94 |
| 2-Acetonyl-3'-chloro-4,5-dimethoxybenzophenone (II) | 1.1 | 0.63 |
| 1-(3-Chlorophenyl)-4-methyl-8-methoxy-5H-2,3-benzodiazepine (IV) | 1.58 | 1.05 |
| 1-(3-Chlorophenyl)-3-methyl-6,7-dimethoxyisoquinoline (V) | 1.46 | 1.37 |

What we claim is:

1. A process for the preparation of 1-(3-chlorophenyl)-4-methyl-7, 8-dimethoxy-5H-2,3-benzodiazepine of formula (I)

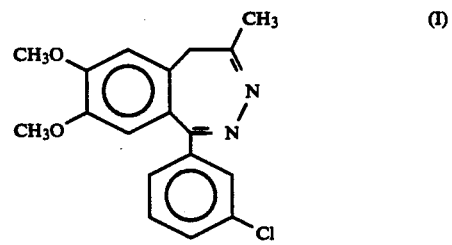

in high purity and in a quality suitable for pharmaceutical purposes, said process comprising reacting 1 mole of 2-acetonyl-3'-chloro-4, 5-dimethoxybenzophenone of formula (II)

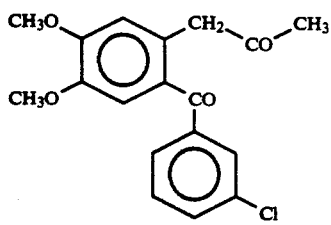 (II)

with 3 to 7 moles of hydrazine hydrate in an organic solvent or in a mixture of organic solvents, at a temperature between 15° C. and 85° C. in the absence of oxygen and optionally in the presence of water, and subsequently recrystallizing the crude product from an aliphatic alcohol containing 1 to 5 carbon atom(s), wherein the total contamination content in said 1-(3-chloro-phenyl)-4-methyl-7, 8-dimethoxy-5H-2,3-benzodiazepine does not exceed 0.3% by mass.

2. A process as claimed in claim 1, which comprises using as solvent a monovalent or polyvalent aliphatic alcohol comprising 1 to 5 carbon atom(s), dimethylformamide, dimethyl sulfoxide, a chlorinated hydrocarbon, peroxide-free dioxane, tetrahydrofuran, the mixtures thereof or—where it is possible—a mixture of these solvents with water.

3. A process as claimed in claim 1, which comprises carrying out the reaction under an atmosphere of nitrogen or a noble gas.

4. A process as claimed in claim 2, which comprises carrying out the reaction under an atmosphere of nitrogen or a noble gas.

* * * * *